(12) United States Patent
Suenaga et al.

(10) Patent No.: US 8,497,358 B2
(45) Date of Patent: Jul. 30, 2013

(54) ANTIBODY PURIFICATION METHOD

(75) Inventors: Masato Suenaga, Yamaguchi (JP); Takeshi Hayakawa, Yamaguchi (JP); Takuya Muramoto, Yamaguchi (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/140,601

(22) PCT Filed: Dec. 18, 2009

(86) PCT No.: PCT/JP2009/071182
§ 371 (c)(1),
(2), (4) Date: Jun. 17, 2011

(87) PCT Pub. No.: WO2010/071208
PCT Pub. Date: Jun. 24, 2010

(65) Prior Publication Data
US 2011/0251374 A1 Oct. 13, 2011

(30) Foreign Application Priority Data
Dec. 19, 2008 (JP) ................................ 2008-324202

(51) Int. Cl.
*C07K 16/00* (2006.01)
*C07K 16/22* (2006.01)

(52) U.S. Cl.
USPC ............ 530/416; 530/412; 530/413; 530/415

(58) Field of Classification Search
None
See application file for complete search history.

(56) References Cited

U.S. PATENT DOCUMENTS

| | | | |
|---|---|---|---|
| 8,017,740 B2 * | 9/2011 | Gagnon | 530/413 |
| 2006/0030696 A1 | 2/2006 | Bonnerjea et al. | |
| 2006/0194953 A1 | 8/2006 | Bonnerjea et al. | |
| 2006/0199948 A1 | 9/2006 | Ejima et al. | |
| 2007/0112178 A1 | 5/2007 | Johansson et al. | |
| 2007/0167613 A1 | 7/2007 | Johansson et al. | |
| 2007/0259453 A1 | 11/2007 | Engstrand et al. | |
| 2008/0019974 A1 | 1/2008 | Kim et al. | |
| 2008/0177048 A1 | 7/2008 | Gagnon | |
| 2008/0312425 A1 | 12/2008 | Bonnerjea et al. | |
| 2010/0278815 A1 | 11/2010 | Kim et al. | |
| 2011/0040075 A1 | 2/2011 | Bonnerjea et al. | |

FOREIGN PATENT DOCUMENTS

| | | |
|---|---|---|
| JP | 2006-242957 | 9/2006 |
| JP | 2008-505851 | 2/2008 |
| JP | 2008-517906 | 5/2008 |
| WO | 2004/076485 | 9/2004 |
| WO | 2005/082926 | 9/2005 |
| WO | 2006/024497 | 3/2006 |
| WO | 2007/115049 | 10/2007 |

OTHER PUBLICATIONS

Arakawa et al., Protein Expression and Purification, 54:110-116, 2007.*
Arakawa, Tsutomu, et al., "MEP chromatography of antibody and Fc-fusion protein using aqueous arginine solution", Protein Expression and Purification, vol. 63, 2009, pp. 158-163.
Sommerfeld, Sven, et al., "Challenges in biotechnology production—generic processes and process optimization for monoclonal antibodies", Chemical Engineering and Processing, vol. 44, 2005, pp. 1123-1137.
Arakawa, T., et al., "Biotechnology applications of amino acids in protein purification and formulations", Amino Acids, vol. 33, 2007, pp. 587-605.
Arakawa, Tsutomu, et al., "Elution of antibodies from a Protein-A column by aqueous arginine solutions", Protein Expression and Purification, vol. 36, 2004, pp. 244-248.
Tsumoto, Kouhei, et al., "Arginine improves protein elution in hydrophobic interaction chromatography, The cases of human interleukin-6 and activin-A", Journal of Chromatography A, vol. 1154, 2007, pp. 81-86.
Tugeu, Nihal, et al., "Maximizing Productivity of Chromatography Steps for Purification of Monoclonal Antibodies", Biotechnology and Bioengineering, vol. 99, No. 3, Feb. 15, 2008, pp. 599-613.
Chen, Jie, et al., "Comparison of standard and new generation hydrophobic interaction chromatography resins in the monoclonal antibody purification process", Journal of Chromatography A, vol. 1177, 2008, pp. 272-281.
Ejima, Daisuke, et al., "Effective elution of antibodies by arginine and arginine derivatives in affinity column chromatography", Analytical Biochemistry, vol. 345, 2005, pp. 250-257.
Ejima, Daisuke, et al., "Arginine as an effective additive in gel permeation chromatography", Journal of Chromatography A, vol. 1094, 2005, pp. 49-55.
Nakakido, Makoto, et al., "Structure-based analysis reveals hydration changes induced by arginine hydrochloride", Biophysical Chemistry, vol. 137, 2008, pp. 105-109.
Tsumoto, Kohei, et al., "Review: Why is Arginine Effective in Suppressing Aggregation?", Protein & Peptide Letters, vol. 12, 2005, pp. 613-619.

* cited by examiner

*Primary Examiner* — Marianne P Allen
(74) *Attorney, Agent, or Firm* — Wenderoth, Lind & Ponack, L.L.P.

(57) ABSTRACT

Provided is a purification method that purifies an antibody to a high purity, effectively removes antibody polymer (or aggregate), and improves antibody recovery rate. An antibody purification method including a step for treating a solution containing an antibody by mixed mode chromatography in the presence of an amino acid is provided.

6 Claims, 1 Drawing Sheet

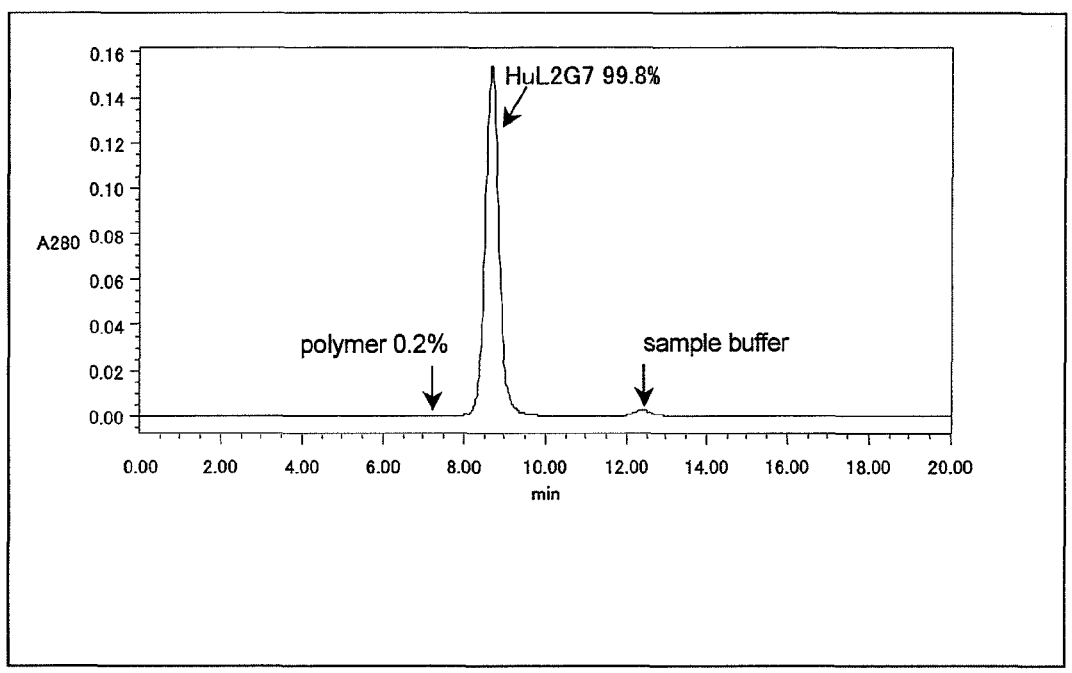

SEQUENCE LISTING

<160> NUMBER OF SEQ ID NOS: 1

<210> SEQ ID NO 1
<211> LENGTH: 12
<212> TYPE: DNA
<213> ORGANISM: Artificial
<220> FEATURE:
<223> OTHER INFORMATION: Synthetic Construct

<400> SEQUENCE: 1
ctcgagacca cc    12

ANTIBODY PURIFICATION METHOD

This application is a U.S. National Stage of International application No. PCT/JP2009/071182, filed Dec. 18, 2009.

TECHNICAL FIELD

The present invention relates to a method of purifying HuL2G7, an antibody against hepatocyte growth factor (HGF).

BACKGROUND OF THE INVENTION

HGF, a hetero-dimer type polypeptide produced by mesenchymal cells, is known to stimulate angiogenesis and the growth and scattering of various cells. The diverse activities of HGF are mediated by the transmembrane tyrosine kinase encoded by the receptor thereof, i.e., the proto-oncogene cMet. HGF/cMet has been reported to play important roles in a broad range of aspects in cancer progression events such as tumorigenesis, invasion and metastasis, apoptosis control and angiogenesis. Therefore, using an antagonist molecule that is effective against HGF is expected to inhibit these biological activities of HGF.

Patent document 1 describes a method of preparing a humanized neutralizing monoclonal antibody against HGF using mouse L2G7mAb.

However, a monoclonal antibody from a tissue culture supernatant, as described in patent document 1, usually contains complex impurity components derived from the cell culture broth; for pharmaceutical use, it is essential to obtain a highly purified antibody deprived of these impurity components. A wide variety of methods of antibody purification have been proposed so far, many of which are based on chromatography. Reported methods of treatment by chromatography are anion exchange chromatography, cation exchange chromatography, and hydrophobic chromatography.

In recent years, affinity chromatography with protein A or protein G has been widely used as a convenient method to obtain high purity in the isolation and purification of antibodies, and is particularly widely known in antibody production on industrial scales.

In another reported method, gel filtration chromatography is performed with an appropriate amount of arginine added to an aqueous buffer solution of a chromatogram developing solvent during treatment of a hydrophobic protein and the like, including an aggregate of associated particles, so as to weaken the possibly occurring unwanted interaction between the protein and the column packing material, whereby an aggregate of associated particles, hydrophobic protein and hydrophobic peptide are more quantitatively recovered (patent document 2).

Patent document 1: WO2007-115049
Patent document JP-A-2006-242957

DISCLOSURE OF THE INVENTION

Problem to be Solved by the Invention

As stated above, a monoclonal antibody obtained from a cell culture supernatant usually contains complex impurity components derived from the cell culture broth used. In addition to these impurity components, there can occur protein association, polymerization, and aggregation in any step for fractional purification, which in turn can contaminate the finally separated antibody. Any polymer once produced is likely to interfere with the operation in the purification step that follows and affect the antibody during its storage, and the polymer can be a cause of adverse reactions during the use of the antibody as a pharmaceutical.

Accordingly, a problem to be solved by the present invention is to provide a method of purifying a monoclonal antibody to high purity, while removing the polymer (or aggregate) of the antibody effectively and improving the antibody recovery rate.

Means of Solving the Problem

Hence, the present inventors diligently investigated the above-described method of purification, found that the above-described problem could be solved by purifying the antibody using a mixed mode resin having both an ion exchange group and a hydrophobic functional group and the like, with the use of an amino acid as an additive, and developed the present invention.

Accordingly, the present invention provides the following:
(1) A method of purifying an antibody, comprising a step for treating a solution containing an antibody in the presence of an amino acid by mixed mode chromatography.
(2) The method of purification according to (1) above, wherein the mixed mode chromatography is preceded by a protein A affinity chromatography treatment step.
(3) The method of purification according to (1) or (2) above, further comprising an ion exchange chromatography treatment step.
(4) The method of purification according to (3) above, wherein the ion exchange chromatography is cation exchange chromatography.
(5) The method of purification according to any one of (1) to (4) above, wherein the amino acid is a basic amino acid, a hydrophobic amino acid, an acidic amino acid or citrulline.
(6) The method of purification according to any one of (1) to (4) above, wherein the amino acid is arginine, histidine, proline, glutamic acid or citrulline.
(7) The method of purification according to any one of (1) to (4) above, wherein the amino acid is a basic amino acid.
(8) The method of purification according to (7) above, wherein the basic amino acid is arginine.
(9) The method of purification according to any one of (1) to (8) above, wherein the antibody is a humanized monoclonal antibody against hepatocyte growth factor (HGF).
(10) The method of purification according to any one of (1) to (8) above, wherein the antibody is a humanized monoclonal antibody of monoclonal antibody L2G7 produced by hybridoma shown by ATCC No.:PTA-5162 against hepatocyte growth factor (HGF).
(11) The method of purification according to any one of (1) to (8) above, wherein the antibody is a humanized monoclonal antibody that competes with monoclonal antibody L2G7 produced by hybridoma shown by ATCC No.:PTA-5162 against hepatocyte growth factor (HGF) for binding to hepatocyte growth factor (HGF).

Effect of the Invention

The present invention employs a step for mixed mode resin treatment in the presence of amino acid in a process of purification of antibodies such as HGF monoclonal antibody, thus making it possible to effectively remove not only the impurity components derived from cell culture broth, but also the polymer (or aggregate) resulting in any other step for purification. The mixed mode resin shows improved polymer-antibody separation capacity by the addition of amino acid to a buffer. As a result, the amount of antibodies treated by the mixed mode resin for removal of polymers can be increased as compared to other resins such as hydrophobic chromatography, hydroxyapatite or gel filtration. Another advantage of the invention resides in the fact that the antibody is recovered as a sharp peak with no elution tailing, and that an excellent recovery rate is achievable. Furthermore, the present invention is highly useful as a method of purification on industrial scales because recovery is possible with a small amount of eluent, production facility can be downsized and the facility construction cost can be reduced.

BRIEF DESCRIPTION OF THE DRAWINGS

FIG. 1 shows the results of an analysis of HuL2G7 by gel filtration HPLC. The arrows indicate the polymer (0.2%), HuL2G7 (99.8%), and the sample buffer, respectively, from the left. Particulars of the operating conditions are given in the text.

DETAILED DESCRIPTION OF THE INVENTION

Humanized Neutralizing Anti-HGF Antibodies

A monoclonal antibody (mAb) that binds to HGF (i.e., an anti-HGF mAb) is said to neutralize HGF, or be neutralizing, if the binding partially or completely inhibits one or more biological activities of HGF. Among the biological properties of HGF that a neutralizing antibody may inhibit, for example, are the ability of HGF to bind to its cMet receptor, to cause the scattering of certain cell lines such as Madin-Darby canine kidney (MDCK) cells; to stimulate proliferation of certain cells including hepatocytes, Mv 1 Lu mink lung epithelial cells, and various human tumor cells; or to stimulate angiogenesis, for example as measured by stimulation of human umbilical vascular endothelial cell (HUVEC) proliferation or tube formation or by induction of blood vessels when applied to the chick embryo chorioallantoic membrane (CAM). A humanized neutralizing antibody preferably binds to human HGF, i.e., to the protein encoded by the GenBank sequence with Accession number D90334. A humanized antibody is a recombinant (monoclonal) antibody in which the CDRs from a mouse antibody ("donor antibody", which can also be antibody of rat, hamster or other similar species) are grafted onto a human antibody ("acceptor antibody").

A humanized neutralizing mAb at a concentration of, e.g., 0.01, 0.1, 0.5, 1, 2, 5, 10, 20 or 50 µg/ml inhibits a biological function of HGF (e.g., stimulation of proliferation or scattering) by about at least 50% but preferably 75% or more, more preferably by 90% or more, or 95% or more, or even 99% or more, and most preferably approximately 100% (essentially completely). Preferably, at least 25%, 50%, 75%, 90%, or 95% or essentially complete inhibition is achieved when the molar ratio of antibody against HGF is 0.1×, 0.5×, 1×, 2×, 3×, 5× or 10×. Most preferably, the mAb neutralizes not just one but several of the biological activities listed above; an anti-HGF mAb that neutralizes all the biological activities of HGF will be called "fully neutralizing", and such mAbs are most preferable. The humanized neutralizing mAb preferably bind specifically to HGF, that is they will not bind, or only bind to a much lesser extent, proteins that are related to HGF such as fibroblast growth factor (FGF) and vascular endothelial growth factor (VEGF).

Humanized neutralizing mAbs include anti-HGF antibodies in their tetrameric form (2 L chains and 2 H chains) and can be of any of the known isotypes IgG, IgA, IgM, IgD and IgE and their subtypes, i.e., IgG1 IgG2, IgG3, IgG4 and may comprise a κ or λ L chain. The humanized neutralizing mAb also include fragments of antibodies such as Fv, Fab and F(ab')$_2$; bifunctional hybrid antibodies, single-chain antibodies; and antibodies with altered constant regions. The source of the CDRs of the mAb may be of animal (e.g., mouse, rat, hamster or chicken) origin, or they may be recombined. Rodent mAbs are made by standard methods well-known in the art, comprising multiple immune sensitization with HGF in appropriate adjuvant i.p., i.v., into the footpad and the like followed by extraction of spleen or lymph node cells and fusion with a suitable immortalized cell line, and then selection for hybridomas that produce antibody binding to HGF.

Humanized forms of the L2G7 mAb encompass most or all of the CDR amino acids from H chain and L chain of L2G7 mAb sequences in human variable region frameworks (including single, composite or consensus sequence human frameworks). For example, some humanized antibodies include three intact CDRs from the L2G7 H chain and three intact CDRs from the L chain. Other humanized antibodies include at least one intact CDR from the L2G7 H chain and at least one intact CDR from the L2G7 L chain. Some humanized antibodies include at least one CDR in which some residues are from the corresponding CDR of L2G7 and the others are from a CDR of a human antibody, preferably the same human antibody as supplies the variable region framework containing the CDR.

In some humanized antibodies at least 1, 3, 5 or all positions selected from the group H29, H30, H48, H66, H67, H71, H94, L3, and L60 are occupied by an amino acid present at the corresponding position by Kabat numbering in the mouse L2G7 antibody. In the human receptor variable region (mentioned below) frameworks (AAC18323 and BAC01726), all of these positions are occupied by human residues differing from the amino acid present at the corresponding position in the mouse L2G7 antibody. Thus, it is preferable to substitute all or most positions selected from the group. If other human variable region frameworks are used, some of the positions may be occupied by amino acids that are the same in the human variable region framework and the mouse L2G7 antibody. Accordingly, substitution is not performed at such positions but can be performed at other positions differing between the human variable region framework and mouse L2G7 antibody in accordance with the rules of Queen. Regardless of the choice of human variable region framework, substitution of other amino acids besides those specified in the above group is also possible. However, in general neither the H chain variable region framework nor the L chain variable region framework of the humanized antibody includes more than ten or twelve substitutions resulting in residues not present in the receptor human variable region framework (including human consensus variable region frameworks and composite human variable region frameworks).

Any constant regions present in the humanized antibodies are human or essentially so, having no more than ten, and preferably two or fewer substitutions relative to a natural human constant region. Some substitutions are advantageous in increasing the half-life of an antibody and/or its affinity for FcγRn. Other substitutions, usually conservative substitutions, are neutral in effect.

Examples of the humanized forms of L2G7 include mature H and L chain variable regions described in FIG. 2 of WO2007/115049. Other preferred forms of humanized L2G7 include mature H and L chain variable regions having sequences at least 90%, 95%, 98% or 99% identical to these sequences (when aligned according to Kabat numbering), and/or differ from them by a small number (typically involving no more than 5 or 10 amino acids) of functionally inconsequential substitutions, deletions and/or insertions. For example, the first amino acid of the H chain may be either Glu or Gln. The substitutions are usually conservative, that is, replacement of an amino acid with one that is chemically similar. For purposes of classifying amino acids substitutions as conservative or nonconservative, amino acids are grouped as follows: Group I (hydrophobic side chains): Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions are those that involve substitutions between amino acids in the same group. Substitutions relative to the variable regions of mouse L2G7 are preferably avoided at positions H29, H30, H48, H66, H67, H71, H94, L3, and L60, where amino acids from mouse L2G7 are included due to the interaction of these positions with CDRs. Substitutions preferably occur in variable region framework positions, but can also occur in CDR regions. If a CDR region is substituted, it is preferable to replace a mouse amino acid with an amino acid from the corresponding position (Kabat numbering) of a human antibody, preferably the same human antibody that supplies the receptor variable region frameworks.

Usually, the humanized L2G7 mAbs are of the IgG1, IgG2, IgG3 or IgG4 isotype with a κ L chain. An IgG1 mAb having the variable regions combined with complete human γ-1 and κ constant region, which is described in FIG. 2 of WO2007/115049, is designated HuL2G7.

Variants of HuL2G7 retaining similar binding characteristics to HuL2G7 can be obtained by mutagenesis followed by mass selection using the phage display methods. Variants are initially selected for specific binding to HGF, optionally in competition with HuL2G7 or mouse L2G7. Variants having the same or similar binding characteristics as dHuL2G7 or mouse 2G7 antibody can then be tested functionally.

Preferred humanized L2G7 mAbs are neutralizing or fully neutralizing against HGF as defined supra. Preferably, for some, most or all biological properties of HGF measured (e.g., binding to Met, stimulation of proliferation of Mv 1 Lu or HUVEC cells), the neutralizing activity of the humanized mAb is within 3-fold, more preferably within 2-fold or 1.5-fold, and most preferably indistinguishable from (i.e., to within experimental error), the neutralizing activity of L2G7 itself. That is, no more than 3-fold, 2-fold, 1.5-fold or the same amount of humanized mAb relative to L2G7 is needed to obtain the same extent of inhibition of the biological property (for example, as measured by IC50's). Preferably, the affinity for HGF of the humanized mAbs is also within 3-fold, 2-fold or essentially indistinguishable from that of L2G7. Similarly, in xenograft mouse models (e.g., using a human glioma cell line such as U87), the humanized mAbs preferably inhibit tumor growth within 3-fold, 2-fold or indistinguishably from the mouse L2G7 mAb. Indeed, preferably only a 40, 20 or even 10 μg dose of humanized mAb administered twice per week completely inhibits growth of U87 tumor xenografts.

Humanized mAbs can be expressed by a variety of art-known methods. For example, genes encoding their L and H chain variable regions may first be synthesized from overlapping oligonucleotides or by PCR mutagenesis of an earlier prepared variant of the desired gene. Because of the degeneracy of the genetic code, a variety of DNA sequences encode each antibody amino acid sequence. However made, the genes encoding the humanized mAb L and H chain genes are inserted together with constant regions into expression vectors (e.g., commercially available from Invitrogen) that provide the necessary regulatory regions, e.g., promoters, enhancers, poly A sites, etc. Use of the CMV promoter-enhancer is preferred. Genes for constant regions are now widely available or may be readily cloned by PCR from human antibody-producing cells. The L and H chain genes may be inserted together into a single vector or into separate vectors. The expression vectors may then be transfected using various art-known methods such as lipofection or electroporation into a variety of mammalian cell lines such as CHO or 293 or non-producing myelomas including Sp2/0 and NS0, and cells expressing the antibodies are selected by appropriate antibiotic selection. Larger amounts of antibody may be produced by growing the cells in commercially available bioreactors.

Once expressed, the humanized mAbs may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and of 98% or 99% or more homogeneity are most preferred, for pharmaceutical uses.

A monoclonal antibody against HGF can be produced through, for example, the steps shown below, which are not to be construed as limiting the method of the present invention.

The first step to humanize L2G7 is to clone its L and H chain genes of L2G7. RNA is prepared from $10^6$ L2G7 (IgG2a, κ) hybridoma cells using an RNeasy Mini Kit (Qiagen) followed by first strand cDNA synthesis with random primers using a kit from Stratagene and addition of dG tails with terminal deoxynucleotidyl transferase (Promega). The H and L chain variable regions are respectively amplified from the cDNA with a primer annealing to the dG tails and a primer annealing to the N-terminal region of Cγ2a for the H chain and a primer annealing to the N-terminal region of Cκ for the L chain, using a high fidelity polymerase AccuPrime Pfx (Invitrogen). Bands of appropriate sizes are gel purified from the PCR products, and sequenced directly or cloned and then sequenced, using the dideoxy termination method with an automated sequencer.

To express a chimeric form of L2G7 and later the humanized mAb, expression vectors similar to the pVk and pVg1 vectors (J. Immunol. 148:1149, 1992) which contain the human Cκ and Cγ1 genes, are constructed from commercially available vectors and DNA fragments. However, the L chain vector has the hyg selectable marker instead of gpt, and the H chain vector has the neo selectable marker instead of Dhfr. The cloned VL and VH genes are subcloned into the appropriate sites of these vectors to generate expression plasmids for the chimeric L2G7 (chL2G7) mAb L and H chain genes. The chL2G7 mAb is produced and shown to bind HGF as well as L2G7 does, proving that correct L and H chain variable regions had been cloned.

To design a humanized L2G7 mAb, the methods of Queen et al. (U.S. Pat. Nos. 5,530,101 and 5,585,089) are generally followed. The National Center for Biotechnology Information (NCBI) database of human antibody sequences is scanned, and the human VH sequence AAC18323 and Vκ sequence BAC01726 are respectively chosen to serve as receptor sequences for the L2G7 VH and VL sequences because the human VH sequence AAC18323 and Vκ sequence BAC01726 have particularly high framework identity to L2G7 VH and VL sequences, respectively. A computer program, Deep View Swiss-Pdb Viewer, available on the worldwide web, is used to construct a molecular model of the L2G7 variable domain, which is used to locate the amino acids in the L2G7 framework that are close enough to the CDRs to potentially interact with them. To design the humanized L2G7 H and L chain variable regions, the CDRs from the mouse L2G7 mAb are first conceptually grafted into the receptor framework regions. At framework positions where the computer model suggests significant contact with the CDRs, which may be needed to maintain the CDR conformation, the amino acids from the mouse antibody are substituted for the original human framework amino acids. For the humanized L2G7 mAb designated HuL2G7, this is done at residues 29, 30 (within Chothia hypervariable loop H1), 48, 66, 67, 71 and 94 of the H chain and at residues 3 and 60 of the L chain, using Kabat numbering. In addition, amino acid 1 of the H chain is replaced with E (Glu) because this amino acid is less likely than Q (Gln) to undergo derivatization in the antibody protein.

The exemplary mAb HuL2G7 discussed in the Examples below has human κ and γ1 constant regions and is therefore an IgG1. However, it is understood that other IgG1 mAb (IgG1, κ) allotypes are encompassed by the designation HuL2G7. Humanized mAbs of isotypes (e.g., IgG2, IgG3 and IgG4) can be made by combining the HuL2G7 variable regions with the appropriate human constant regions. Replacements can be made in the HuL2G7 constant regions to reduce or increase effector function such as complement-mediated cytotoxicity or ADCC, or to prolong half-life in humans. Specifically but without limitation, HuL2G7 having mutations in the IgG constant region to a Gln at position 250 and/or a Leu at position 428 are mentioned as Examples.

Having designed the HuL2G7mAb, i.e., having chosen the amino acid sequences of its L and H chain variable regions, DNA sequences encoding the variable regions (including signal peptides) are routinely chosen via the genetic code; the sequences begin with CTCGAGACCACC (SEQ ID NO: 1) before the ATG start codon to provide a restriction site for cloning and a Kozak translation initiation signal. These genes are synthesized commercially by Genscript Corp. (Piscataway, NJ). Briefly, two pairs of overlapping oligonucleotides on alternating strands are synthesized (Applied Biosystems DNA synthesizer), which together encompass the entire gene. The oligonucleotides are 110 to 140 bases long with 15-base overlaps. Double-stranded DNA fragments are synthesized using Klenow polymerase from the 5' pair of oligos and separately from the 3' pair. The 5' DNA fragment is cleaved with the restriction enzymes cutting at the 5' end and at the center of the variable region gene. The 3' DNA fragment is cleaved with the restriction enzymes cutting at the center and at the 3' end of the variable region gene. Each cleaved fragment is inserted into a suitable cloning vector and transformed into E. coli, and DNA from a number of isolates is sequenced to find fragments that have completely correct sequences. For each gene, a 3-way ligation is then performed to insert the correct 5' and 3' fragments into the appropriate expression vector to form the complete gene, the sequence of which is verified.

To produce the HuL2G7 mAb, human renal epithelial 293-F cells (Invitrogen) are cultured in Freestyle293 expression medium (FS medium; Invitrogen) and resuspended in FS medium at $10^6$ cells/2 ml/microwell. The HuL2G7 L and H chain expression vector DNAs (1 μg of each) are incubated with 3 μl of Fugene 6 (Roche) in 100 μl FS medium for 30 min at RT; the mixture is then added to the cells. After 48 hr incubation, transfected cells are cultured in the presence of 1 mg/ml G418 to select for cells expressing the neomycin resistant gene and then spread into 96-well tissue culture plates (100 μl/well). After approximately 2 weeks, when wells containing viable cells become confluent, culture supernatants from those wells are tested for the presence and quantity of HuL2G7 by ELISA. Transfected cells may secrete an imbalance of L and H chains, so to ensure that only complete HuL2G7 is measured, this ELISA uses goat anti-human Fc as a capture agent and biotinylated anti-human κ as a detection reagent. The chL2G7 mAb is expressed similarly. Clones of cells expressing relatively high levels of ChL2G7 and HuL2G7 are respectively expanded and grown in FS medium. Antibody is purified from culture supernatants using protein A affinity chromatography and analyzed for purity by SDS-PAGE.

More specifically, as HuL2G7mAb, a humanized monoclonal antibody of monoclonal antibody L2G7 produced by hybridoma shown by ATCC No.:PTA-5162, which is used in the below-mentioned Example 1 and the like, is preferably used. Furthermore, a humanized monoclonal antibody that competes with monoclonal antibody L2G7 produced by hybridoma shown by ATCC No.:PTA-5162 for binding to HGF is also used preferably. HuL2G7mAb can be produced, for example, according to the method described in PCT/US2007/065385 (WO2007/115049).

The method of purification according to the present invention comprises a step for treating a culture supernatant containing an antibody such as the above-mentioned humanized monoclonal antibody against HGF (e.g., polyclonal antibody, monoclonal antibody, humanized antibody, human antibody, chimeric antibody and the like, against antigen such as HGF etc.) with a mixed mode resin in the presence of a basic amino acid at a stage during the purification to further purify the antibody to obtain the same with high purity.

Various methods of purification such as protein A affinity chromatography, anion exchange chromatography, and cation exchange chromatography can be used before or after the mixed mode resin treatment. In particular, it is preferable to perform protein A affinity chromatography treatment in a step preceding the mixed mode resin treatment.

The antibody-containing liquid obtained through the various purification steps may be passed through a membrane filter for concentration as required.

For the operation and treatment in each chromatography, any publicly known methods can be used.

The mixed mode resin used in the present invention is a chromatography resin consisting of a carrier with a multimodal ligand immobilized thereon, the ligand comprising one or more anion or cation exchange groups and one or more aromatic or heterocyclic aromatic systems, and is commercially available as, e.g., Capto adhere (GE Healthcare), Capto MMC (GE Healthcare), and MEP HyperCel (PALL).

Protein A affinity chromatography can be performed by means of, for example, MabSelect SuRe (GE Healthcare) and ProSep Ultra Plus (Millipore).

The ion exchange resin used, whether for anion exchange chromatography or cation exchange chromatography, is preferably a cation chromatography resin, exemplified by Capto S (GE Healthcare), UNOsphere S (Bio-Rad Laboratories), Fractogel SE Hicap (M) (Merck KGaA), Q and CM Ceramic HyperD (PALL).

Examples of the amino acid to be present in the treatment step with mixed mode resin include basic amino acids (e.g., arginine, histidine, lysine), hydrophobic amino acids (e.g., proline), acidic amino acids (e.g., glutamic acid, aspartic acid), citrulline, and/or a derivative thereof. Of these, basic amino acids such as arginine, lysine, histidine and the like are preferable, and arginine and/or a derivative thereof are more preferable.

The amino acid may be present in the antibody solution to be applied to the mixed mode resin, or may be contained in the developing solvent.

The content amount of the amino acid is 1 mM to 1 M, preferably 10 mM to 500 mM, in the antibody solution, and 1 mM to 1 M, preferably 10 mM to 500 mM, in the developing solvent.

The amino acid may be present in a step of purification other than the mixed mode resin treatment step. In that case, the content amount and concentration are the same as those described above.

The amino acid to be added may be in the form of a water-soluble salt.

The developing solvent includes a citrate buffer, an acetate buffer, a carbonate buffer, a phosphate buffer or the like. The developing solvent is preferably a citrate buffer.

The concentration of amino acid (particularly arginine) in the developing solvent is preferably 10 mM to 500 mM, more preferably 50 mM to 350 mM.

Therapeutic Methods

In a preferred embodiment, the humanized antibody provides a pharmaceutical formulation comprising itself. Pharmaceutical formulations of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make themselves isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art. The mAb is typically present at a concentration of 1-100 mg/ml, e.g., 10 mg/ml.

In another preferred embodiment, it provides a method of treating a patient with a disease using a humanized anti-HGF mAb such as humanized L2G7, e.g., HuL2G7, in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease, or encapsulated into carrying agents such as liposomes. The dose given is sufficient to alleviate the condition being treated ("therapeutically effective dose") and is likely to be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/m². Usually between 1 and 8 doses, (e.g., 1, 2, 3, 4, 5, 6, 7 or 8) are administered to treat cancer, but 10, 20 or more doses may be given. The mAb can be administered daily, biweekly, weekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration.

Diseases especially susceptible to therapy with the humanized anti-HGF mAbs, e.g., HuL2G7, include solid tumors believed to require angiogenesis or to be associated with elevated levels of HGF, for example ovarian cancer, breast cancer, lung cancer (small cell or non-small cell), colon cancer, prostate cancer, pancreatic cancer, gastric cancer, liver cancer, head-and-neck tumors, melanoma and sarcomas of children or adults, and brain tumors. Indeed, a therapeutic method for cancer with mAb, especially systemic treatment with a humanized L2G7 mAb, are especially applicable to the treatment of brain tumors including meningiomas; gliomas including ependymomas, oligodendrogliomas, and all types of astrocytomas (low grade, anaplastic, and glioblastoma multiform or simply glioblastoma); medulloblastomas, gangliogliomas, schwannomas, chordomas; and brain tumors primarily of children including primitive neuroectodermal tumors. Both primary brain tumors and secondary or metastatic brain tumors can be treated by the methods. Other diseases suitable for treatment by the methods are those associated with undesired angiogenesis such as diabetic retinopathy, age-related muscular degeneration, rheumatoid arthritis and psoriasis.

In an especially preferred embodiment, the humanized anti-HGF mAb, e.g., HuL2G7, is administered together with (i.e., before, during or after) other anticancer therapy. For example, the mAb may be administered together with any one or more of the chemotherapeutic drugs known to those skilled in the art of oncology, for example alkylating agents such as carmustine, chlorambucil, cisplatin, carboplatin, oxiplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; agents specifically approved for brain tumors including temozolomide and Gliadel® wafer containing carmustine; and other drugs including irinotecan and Gleevec® and all approved and experimental anti-cancer agents. Other agents with which the humanized anti-HGF mAb can be administered include biologics such as monoclonal antibodies, including Herceptin™ against the HER2 antigen, Avastin™ against VEGF, or antibodies to the EGF receptor, as well as small molecule anti-angiogenic or EGF receptor antagonist drugs. In addition, the humanized anti-HGF mAb can be used together with radiation therapy or surgery.

Treatment (e.g., standard chemotherapy) including the humanized anti-HGF mAb antibody (e.g., HuL2G7), can increase the median progression-free survival or overall survival time of patients with these tumors (e.g., ovarian, breast, lung, pancreas, brain and colon, especially when relapsed or refractory) by at least 30% or 40% but preferably 50%, 60% to 70% or even 100%, compared to the same treatment (e.g., chemotherapy) but without anti-HGF mAb. In addition or alternatively, treatment (e.g., standard chemotherapy) including the anti-HGF mAb can increase the complete response rate, partial response rate, or objective response rate (complete+partial) of patients with these tumors (e.g., ovarian, breast, lung, pancreas, brain and colon, especially when relapsed or refractory) by at least 30% or 40% but preferably 50%, 60% to 70% or even 100% compared to the same treatment (e.g., chemotherapy) but without the anti-HGF mAb. For brain tumors such as glioblastomas, treatment with the humanized anti-HGF mAb, alone or in combination with other agents, preferably provides a partial, complete or objective response rate of at least 5% or 10%, more preferably 20% or 25% or 30%, and most preferably 40%, 50% or higher.

In a clinical trial, the aforementioned increases in median progression-free survival and/or response rate of the patients treated with standard therapy plus the humanized anti-HGF mAb (e.g., HuL2G7), relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

Other Methods

The humanized anti-HGF mAbs also find use in diagnostic, prognostic and laboratory methods. They may be used to measure the level of HGF in a tumor or in the circulation of a patient with a tumor, and therefore to follow and guide treatment of the tumor. For example, a tumor associated with high levels of HGF would be especially susceptible to treatment with a humanized anti-HGF mAb. In particular embodiments, the mAbs can be used in an ELISA or radioimmunoassay to measure the level of HGF, e.g., in a tumor biopsy specimen or in serum or in media supernatant of HGF-secreting cells in cell culture. For various assays, the anti-HGF mAb may be labeled with fluorescent molecules, spin-labeled molecules, enzymes or radioisotopes, and may be provided in the form of kit with all the necessary reagents to perform the assay for HGF. In other uses, the anti-HGF mAbs are used to purify HGF, e.g., by affinity chromatography.

The present invention is hereinafter described in further detail by means of the following Examples, which, however, are for illustrative purposes only and do not limit the scope of the invention in any way.

EXAMPLES

Example 1

Purification of HuL2G7

1. Preparation of Cell Culture Broth

An expression vector incorporating a gene that encodes an antibody against hepatocyte growth factor (PCT/US2007/065385; WO2007/115049) was transfected to Chinese hamster ovarian cells to acquire a cell line that produces HuL2G7, an antibody against hepatocyte growth factor. This antibody-producing cell line was cultured in a modified CD-CHO (Invitrogen) medium to yield about 10 L of cell culture broth.

2. Preparation of Cell Culture Broth Supernatant

The cell culture broth supernatant containing HuL2G7 obtained in 1 above was filtered through a depth filter (Millistak+HC mini) (Millipore), and the filtrate was further filtered through a 0.2 μm membrane filter (Sartolab P plus, Sartorius stedim).

3. Protein A Affinity Chromatography

The 1008 mL (HuL2G7: 3,956 mg) of filtrate obtained in 2 above was applied to a MabSelect SuRe column (30 mm ID×200 mm L, GE Healthcare) equilibrated with a buffer (50 mM Tris-HCl buffer containing 100 mM NaCl, pH 7.5), and the column was washed with the same buffer. The proteins were eluted with 50 mM citrate buffer (pH 3.2) and the desired farction was pooled (pooled liquid volume: 279 mL, HuL2G7: 3,814 mg, monomer purity: 82.4%, polymer: 17.6%).

4. Virus Inactivation

The eluate of protein A column obtained in 3 above was adjusted with 0.1 N hydrochloric acid to pH 3.5, and stirred at room temperature for 1 hour. Subsequently, the eluate was adjusted with 1 M Tris to pH 5.0, and filtered through a 0.2 μm membrane filter (Sartolab P plus, Sartorius stedim).

5. Buffer Exchange by Cross-flow Filtration

The buffer of filtrate obtained in 4 above was exchanged with a buffer (20 mM citric acid, 87.5 mM L(+)-arginine, pH 6.2) using the Saltocon slice 200 membrane (exclusion cutoff molecular weight: 30 kDa, Sartorius stedim), followed by filtration through a 0.2 μm membrane filter (Sartolab P plus, Sartorius stedim).

6. Mixed Mode Chromatography

After 47.6 mL HuL2G7 solution obtained by buffer exchange in 5 above (HuL2G7 content: 785 mg) was applied to a Capto adhere column (10 mm ID×200 mm, GE Healthcare) equilibrated with a buffer (20 mM citric acid, 87.5 mM L(+)-arginine, pH 6.2), the buffer (20 mM citric acid, 87.5 mM L(+)-arginine, pH 6.2) was passed through the column, and the desired fraction was pooled (pooled liquid volume: 182 mL, HuL2G7: 639 mg, monomer purity: 96.2%, polymer content: 3.8%).

7. Buffer Exchange by Cross-flow Filtration

The buffer of HuL2G7 solution obtained in the step 6 above was exchanged with a buffer (20 mM citric acid, 14 mM NaCl, pH 5.0) in the same manner as 5 above, and filtered through a 0.2 μm membrane filter (Sartolab P plus, Sartorius stedim).

8. Cation Exchange Chromatography 18.8 mL (HuL2G7: 70 mg) of the HuL2G7 solution obtained in the step 7 above was applied to a HiTrap Capto S column (7 mm ID×25 mm L, GE Healthcare) equilibrated with a buffer (20 mM citric acid, 14 mM NaCl, pH 5.0), and the column was washed with the same buffer. The proteins were eluted with a 20 mM citrate buffer (pH 5.0) containing 85 mM NaCl, and the desired farction was pooled (pooled liquid volume: 19 mL, HuL2G7: 61.9 mg, monomer purity: 99.8%, polymer: 0.2%).

The HuL2G7 recovery rate for the entire purification process was 69.4%.

Analytical Procedures

1. Determination of HuL2G7 Concentration by HPLC

The HuL2G7 concentration in the filtrate was determined using a PA ID sensor cartridge (2.1 mm ID×30 mm L, Applied Biosystems).

2. HuL2G7 Monomer Analysis by Gel Filtration HPLC

A 12.3 μL sample of the HuL2G7 obtained in the (step) 8 above (HuL2G7 Capto S eluted fraction 40 μg) was applied to a TSKgel G3000 SWXL column (7.8 mm ID×300 mm L, Tosoh Corporation) equilibrated with a 200 mM potassium phosphate buffer (pH 6.9) containing 150 mM KCl, followed by passage of the same buffer at a flow rate of 1 mL/min for 20 minutes, and monitoring the absorbance at 280 nm, whereby the polymer and monomer contents were analyzed.

Example 2

Purification of HuL2G7

1. Preparation of Cell Culture Medium

An expression vector incorporating a gene (PCT/US2007/065385; WO2007/115049) encoding an antibody against hepatocyte growth factor was transfected into Chinese hamster ovary cell to give a cell line that produces HuL2G7, an antibody against hepatocyte growth factor. This production cell line was cultured in a modified CD-CHO (Invitrogen) medium to give about 10 L of a cell culture medium.

2. Preparation of Cell Culture Medium Supernatant

The supernatant of the cell culture medium containing HuL2G7 obtained in the above-mentioned 1 was passed through a depth filter (Millistak+HC, Millipore), and the filtrate was further filtered through a 0.2 μm membrane filter and then transferred to a disposable bag (Flexboy 10 L, Sartorius stedim).

3. Protein A Affinity Chromatography

The filtrate (7,749 L, HuL2G7:43,278 mg) obtained in the above-mentioned 2 was applied to MabSelect SuRe column (100 mm ID×200 mm L, GE Healthcare) equilibrated with a buffer (50 mM Tris-HCl buffer containing 100 mM NaCl, pH 7.5), washed with the same buffer and eluted with a 50 mM citrate buffer (pH 3.2). The desired fraction containing HuL2G7 was pooled (amount of pooled liquid: 1850 L, HuL2G7: 38,546 mg, monomer purity: 93%).

4. Virus Inactivation

The eluate of protein A column obtained in the above-mentioned 3 was adjusted to pH 3.5 with 0.1N hydrochloric acid, and the eluate was stirred at room temperature for 1 hr. Thereafter, the eluate was adjusted to pH 5.0 with 1M Tris, and passed through a 0.2 µm membrane filter (sartopore2, Sartorius stedim). Two days later, the filtrate was further passed through a 0.65 µm depth filter (sartopure GF, Sartorius stedim), and a 0.2 µm membrane filter (sartopore2, Sartorius stedim).

5. Buffer Exchange by Gel Filtration Chromatography Column

The buffer of the filtrate (5 mL) obtained in the above-mentioned 4 was exchanged with 20 mM citrate buffer (pH 6.0) containing 350 mM proline by Sephadex G-25 gel filtration column (PD-10 Desalting column, GE Healthcare), and the filtrate was passed through a 0.2 µm membrane filter (Millex GV filter unit, Millipore).

6. Purification by Mixed Mode Chromatography

The HuL2G7 solution (4.4 mL, HuL2G7: 50 mg) after substitution with the buffer containing 350 mM proline in the above-mentioned 5 was applied to Capto adhere column (Hi-Trap Capto adhere 1 mL, GE Healthcare) equilibrated with 20 mM citrate buffer (pH 6.0) containing 350 mM proline. The buffer used for the equilibration was applied and the fraction that passed through was pooled (amount of pooled liquid: 11.5 mL, HuL2G7: 43 mg, monomer purity: 98%).

7. Buffer exchange by gel filtration chromatography column

The HuL2G7 solution obtained in the above-mentioned 6 was concentrated to 5 mL with a centrifugal filter (Amicon Ultra-0.5, Ultracel-30, 30 kDa, Millipore), the buffer was exchanged with 20 mM citrate buffer (pH 5.0) in the same manner as in the above-mentioned 5, and the solution was passed through a 0.2 µm membrane filter (Millex GV filter unit, Millipore).

8. Cation Exchange Chromatography

The HuL2G7 solution (6.4 mL, HuL2G7: 32 mg) after the buffer substitution in the above-mentioned 7 was applied to Capto S column (HiTrap Capto S 1 mL, GE Healthcare) equilibrated with a 20 mM citrate buffer (pH 5.0). The same buffer used for the equilibration was applied and the fraction that passed through was pooled (amount of pooled liquid: 18.2 mL, HuL2G7: 26.34 mg, monomer purity: 100%).

Example 3

Purification of HuL2G7

1. Preparation of Cell Culture Medium

An expression vector incorporating a gene (PCT/US2007/065385; WO2007/115049) encoding an antibody against hepatocyte growth factor was transfected into Chinese hamster ovary cell to give a cell line that produces HuL2G7, an antibody against hepatocyte growth factor. This production cell line was cultured in a modified CD-CHO (Invitrogen) medium to give about 10 L of a cell culture medium.

2. Preparation of Cell Culture Medium Supernatant

The supernatant of the cell culture medium containing HuL2G7 obtained in the above-mentioned 1 was passed through a depth filter (Millistak+HC, Millipore), and the filtrate was further filtered through a 0.2 µm membrane filter and then transferred to a disposable bag (Flexboy 10 L, Sartorius stedim).

3. Protein A Affinity Chromatography

The filtrate (7,749 L, HuL2G7:43,278 mg) obtained in the above-mentioned 2 was applied to MabSelect SuRe column (100 mmID×200 mmL, GE Healthcare) equilibrated with a buffer (50 mM Tris-HCl buffer containing 100 mM NaCl, pH 7.5), washed with the same buffer and eluted with a 50 mM citrate buffer (pH 3.2). The desired fraction containing HuL2G7 was pooled (amount of pooled liquid: 1850 L, HuL2G7: 38,546 mg, monomer purity: 93%).

4. Virus Inactivation

The eluate of protein A column obtained in the above-mentioned 3 was adjusted to pH 3.5 with 0.1N hydrochloric acid, and the eluate was stirred at room temperature for 1 hr. Thereafter, the eluate was adjusted to pH 5.0 with 1M Tris, passed through a 0.2 µm membrane filter (sartopore2, Sartorius stedim) and stored at 5° C. Two days later, the filtrate was passed through a 0.65 µm depth filter (sartopure GF, Sartorius stedim), and a 0.2 µm membrane filter (sartopore2, Sartorius stedim).

5. Buffer Exchange by Gel Filtration Chromatography Column

The buffer of the filtrate (5 mL) obtained in the above-mentioned 4 was substituted with 4 kinds of 20 mM citrate buffers (pH 6.0) containing 375 mL each of glycine (Gly, neutral amino acid), histidine (His, basic amino acid), glutamic acid (Glu, acidic amino acid), proline (Pro, hydrophobic amino acid), respectively, by Sephadex G-25 gel filtration column (PD MiniTrap G-25, GE Healthcare). Each solution after the buffer substitution was diluted with each buffer to 5 mg/mL, and passed through a 0.2 µm membrane filter (Millex GV filter unit, Millipore).

6. Purification by Mixed Mode Chromatography

A 96-well PreDictor Capto adhere (2 µL, GE Healthcare) was equilibrated with 4 kinds of 20 mM citrate buffers (pH 6.0) containing each amino acid shown in the above-mentioned 5 (1 well for each buffer), and the HuL2G7 solution obtained in the above-mentioned 5 (200 µL, HuL2G7: 1 mg) was applied. The same buffer used for the equilibration was applied and the desired fraction that passed through was pooled. In the case of buffer free of amino acid, the recovery rate was 43%, and the monomer purity was 96%. In the case of a 20 mM citrate buffer containing 375 mM glycine, the recovery rate was 55%, and the monomer purity was 96%. In the case of a citrate buffer containing 375 mM histidine, the recovery rate was 97%, and the monomer purity was 95%. In the case of a buffer containing 375 mM glutamic acid, the recovery rate was 93%, and the monomer purity was 95%. In the case of a buffer containing 375 mM proline, the recovery rate was 84%, and the monomer purity was 96%.

This application is based on a patent application No. 2008-324202 filed in Japan (filing date: Dec. 19, 2008), the contents of which are incorporated in full herein.

The invention claimed is:

1. A method for purifying an antibody, comprising:
a step of contacting a buffer containing an antibody and 10 mM to 500 mM of an amino acid with a mixed mode chromatography resin, and
a step of collecting a flow-through fraction containing a purified antibody having a reduced antibody aggregate content, wherein:
the mixed mode chromatography resin comprises an ion exchange group and a hydrophobic group, and
the amino acid is selected from the group consisting of arginine, histidine, proline, glutamic acid and citrulline.

2. The method according to claim 1, wherein the contacting step is preceded by a protein A affinity chromatography treatment step.

3. The method according to claim 1, wherein the collecting step is followed by an ion exchange chromatography treatment step.

4. The method according to claim 3, wherein the ion exchange chromatography is cation exchange chromatography.

5. The method according to claim 1, wherein the amino acid is arginine.

6. The method according to claim 1, wherein the antibody is a humanized monoclonal antibody against hepatocyte growth factor (HGF).

* * * * *